(12) United States Patent
Krivoruchko et al.

(10) Patent No.: US 7,651,527 B2
(45) Date of Patent: Jan. 26, 2010

(54) BIORESORBABLE STENT

(75) Inventors: Micheal Krivoruchko, Forestville, CA (US); Jeffrey Allen, Santa Rosa, CA (US); Matthew Birdsall, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 206 days.

(21) Appl. No.: 11/611,533

(22) Filed: Dec. 15, 2006

(65) Prior Publication Data

US 2008/0147175 A1 Jun. 19, 2008

(51) Int. Cl.
*A61F 2/06* (2006.01)

(52) U.S. Cl. .................. 623/1.38; 623/1.44; 623/1.45

(58) Field of Classification Search ....... 623/1.38–1.46; A61F 2/06
See application file for complete search history.

(56) References Cited

U.S. PATENT DOCUMENTS

| | | | |
|---|---|---|---|
| 6,287,332 B1 | 9/2001 | Bolz et al. | |
| 6,981,987 B2 | 1/2006 | Huxel et al. | |
| 2002/0004060 A1 | 1/2002 | Heublein et al. | |
| 2004/0034409 A1 | 2/2004 | Heublein et al. | |
| 2004/0098108 A1 | 5/2004 | Harder et al. | |
| 2004/0158318 A1* | 8/2004 | Matson | 623/1.46 |
| 2006/0229711 A1 | 10/2006 | Yan et al. | |
| 2006/0271168 A1* | 11/2006 | Kleine et al. | 623/1.38 |

FOREIGN PATENT DOCUMENTS

| | | |
|---|---|---|
| DE | 19856983 | 12/1999 |
| WO | WO03/063733 | 8/2003 |

* cited by examiner

*Primary Examiner*—Corrine M McDermott
*Assistant Examiner*—Jason-Dennis Stewart

(57) ABSTRACT

A bioresorbable endoluminal prosthesis for placement in a body lumen having a stent substrate of a first metallic material that has a lower electrical potential than a standard reference electrode. The stent substrate is coated with a biodegradable polymer having a second metallic material dispersed therein, wherein the second metallic material has a higher electrical potential than the standard reference electrode. After implantation of the stent within the body lumen, the second metallic material is present in the polymeric coating in a sufficient concentration to cause galvanic corrosion of the first metallic material such that over time the stent substrate is bioresorbed.

12 Claims, 1 Drawing Sheet

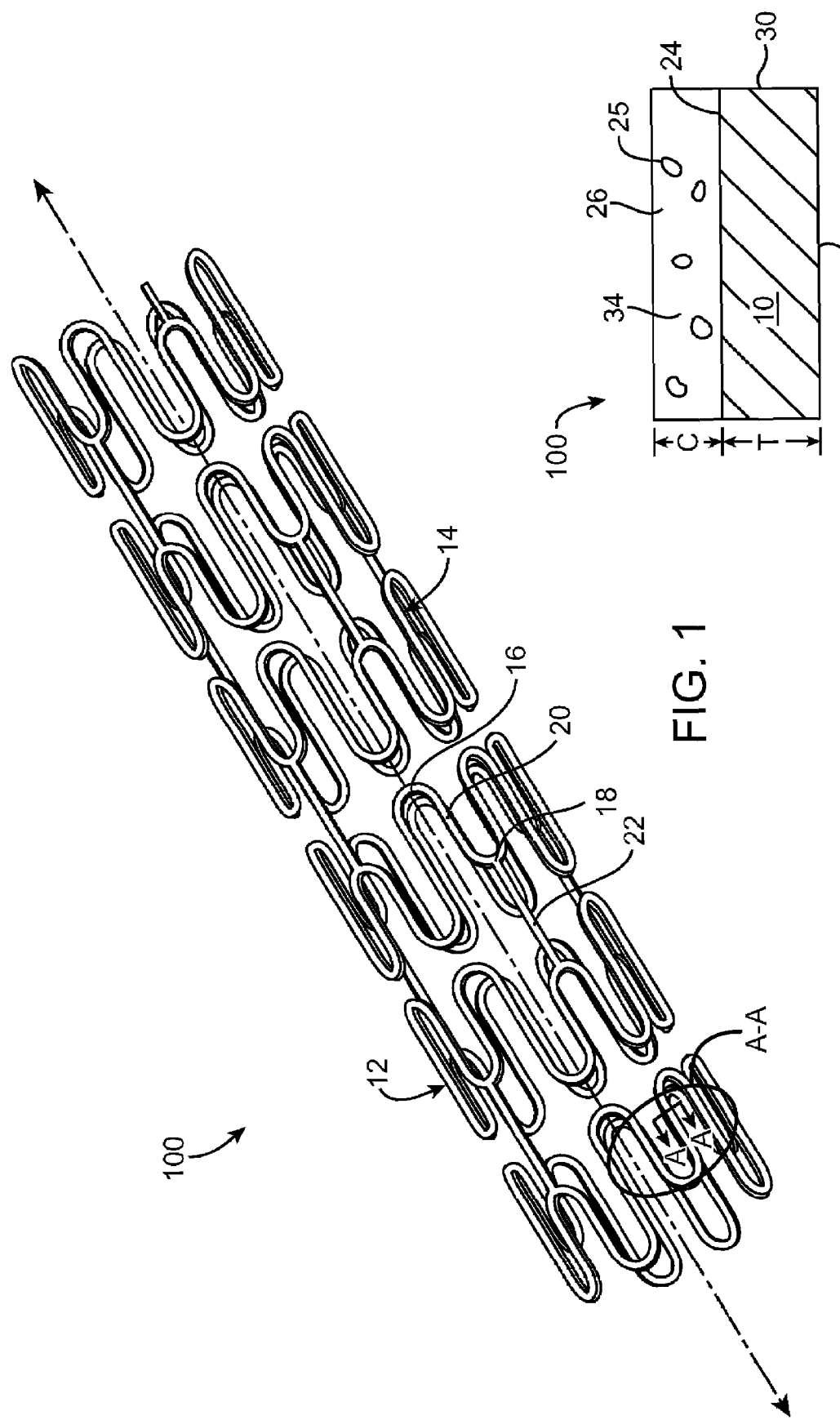

BIORESORBABLE STENT

FIELD OF THE INVENTION

The invention relates generally to temporary endoluminal prostheses for placement in a body lumen, and more particularly to stents that are bioresorbable.

BACKGROUND OF THE INVENTION

A wide range of medical treatments exist that utilize "endoluminal prostheses." As used herein, endoluminal prostheses is intended to cover medical devices that are adapted for temporary or permanent implantation within a body lumen, including both naturally occurring and artificially made lumens, such as without limitation: arteries, whether located within the coronary, mesentery, peripheral, or cerebral vasculature; veins; gastrointestinal tract; biliary tract; urethra; trachea; hepatic shunts; and fallopian tubes.

Accordingly, a wide assortment of endoluminal prostheses have been developed, each providing a uniquely beneficial structure to modify the mechanics of the targeted lumen wall. For example, stent prostheses are known for implantation within body lumens to provide artificial radial support to the wall tissue, which forms the various lumens within the body, and often more specifically, for implantation within the blood vessels of the body.

Essentially, stents that are presently utilized are made to be permanently or temporarily implanted. A permanent stent is designed to be maintained in a body lumen for an indeterminate amount of time and is typically designed to provide long term support for damaged or traumatized wall tissues of the lumen. There are numerous conventional applications for permanent stents including cardiovascular, urological, gastrointestinal, and gynecological applications. A temporary stent is designed to be maintained in a body lumen for a limited period of time in order to maintain the patency of the body lumen, for example, after trauma to a lumen caused by a surgical procedure or an injury.

Permanent stents, over time, may become encapsulated and covered with endothelium tissues, for example, in cardiovascular applications, causing irritation to the surrounding tissue. Further, if an additional interventional procedure is ever warranted, a previously permanently implanted stent may make it more difficult to perform the subsequent procedure.

Temporary stents, on the other hand, preferably do not become incorporated into the walls of the lumen by tissue ingrowth or encapsulation. Temporary stents may advantageously be eliminated from body lumens after an appropriate period of time, for example, after the traumatized tissues of the lumen have healed and a stent is no longer needed to maintain the patency of the lumen. As such, temporary stents may be removed surgically or be made bioabsorbable/biodegradable.

Temporary stents may be made from bioabsorbable and biodegradable materials that are selected to absorb or degrade in vivo over time. However, there are disadvantages and limitations associated with the use of bioabsorbable or biodegradable stents. Many bioabsorbable or biodegradable materials have insufficient mechanical strength or other properties, such as a lack of plastic deformability, to perform adequately under the loading conditions within a treatment location upon implantation. Other limitations arise in controlling the break down of the bioabsorbable materials from which such stents are made, as in, preventing the material from breaking down too quickly or too slowly. If the material is absorbed too quickly, the stent will not provide sufficient time for the vessel to heal, or if absorbed too slowly, the attendant disadvantages of permanently implanted stents may arise.

In order to obtain the ideal properties for a bioresorbable vascular implant, the implant must have sufficient mechanical properties to withstand the loading conditions within the treatment location upon implantation. This requires a high degree of mechanical strength initially upon acute implantation to resist forces exerted on the implant by the surrounding tissue. However, due to the dynamic healing response of the body these forces decrease over time as the surrounding tissue remodels. This remodeling process begins immediately after implantation and may continue for several months, even years. From a stent design viewpoint, there is a point in time at which the remodeling process has achieve sufficient mechanical scaffolding to prevent undesirable clinical recoil or collapse without the need of a metallic implant. It is therefore desirable to have a vascular implant with a high degree of mechanical strength initially, but diminishing strength as time proceeds. Accordingly, there is a need for a temporary stent that provides sufficient support in a body lumen for the duration of a therapeutically appropriate period of time, which then degrades to be eliminated from the patient's body without surgical intervention.

BRIEF SUMMARY OF THE INVENTION

An embodiment of the present invention is a bioresorbable endoluminal prosthesis for placement in a body lumen. The endoluminal prosthesis includes a stent substrate of a first metallic material that has a lower electrical potential than a standard reference electrode. The stent substrate is coated with a biodegradable polymer having a second metallic material dispersed therein, wherein the second metallic material has a higher electrical potential than the standard reference electrode. After implantation of the stent within the body lumen, the second metallic material is present in the polymeric coating in a sufficient particulate density or count to cause galvanic corrosion of the first metallic material, such that over time the stent substrate is bioresorbed.

BRIEF DESCRIPTION OF DRAWINGS

The foregoing and other features and advantages of the invention will be apparent from the following description of the invention as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1 a perspective view of an exemplary stent in accordance with an embodiment of the present invention.

FIG. 2 is a schematic cross-sectional view of a stent strut taken along line A-A of FIG. 1 showing a coating in accordance with an embodiment of the present invention.

DETAILED DESCRIPTION OF THE INVENTION

An embodiment of the present invention includes a bioresorbable stent that utilizes a metal impregnated polymeric coating to control degradation and bioresorption of a metallic substrate of the stent. A stent that is "bioresorbable" is one that will gradual breakdown and disperse in the circulation and thereby be removed from supporting, or otherwise residing in, a body lumen. In an embodiment, the stent substrate or framework is formed into its desired shape from a tube, sheet or wire of a first metallic material, wherein the first metallic material possesses the requisite mechanical properties for forming a stent that is deliverable and implantable within a body lumen. The first metallic material is also selected to be an "active" material, which is a material that has a lower or negative electrical potential relative to a standard reference electrode, such as a saturated calomel electrode (SCE).

The "active" stent substrate is then coated with a biodegradable polymer that has a second metallic material dispersed therein. In an embodiment, the second metallic material may be dispersed within the biodegradable polymer in the form of a powder. The second metallic material is selected to be a passive or noble material, which is a material that has a higher electrical potential relative to a standard reference electrode, for example, an electrical potential higher than the 0.241 V of a SCE. The second metallic material is present in the biodegradable polymer in a sufficient particulate density/number or concentration by weight so as to promote galvanic corrosion of the first metallic material of the stent substrate upon, or some specified time after, implantation of the stent within a body lumen. Due to the galvanic corrosion, the stent substrate will then degrade or corrode over a therapeutically appropriate period of time to eventually be eliminated from the body lumen. In an embodiment, the stent structure is bioresorbed first with the biodegradable coating fully degrading thereafter, such that no portion of the stent remains within the body lumen.

FIGS. 1 and 2 illustrate an endoluminal prosthesis in accordance with an embodiment of the present invention. Stent 100 is a patterned tubular device that includes a plurality of radially expandable cylindrical rings 12. Cylindrical rings 12 are formed from struts 14 formed in a generally sinusoidal pattern including peaks 16, valleys 18, and generally straight segments 20 connecting peaks 16 and valleys 18. Connecting links 22 connect adjacent cylindrical rings 12 together. In FIG. 1, connecting links 22 are shown as generally straight links connecting peak 16 of one ring 12 to valley 18 of an adjacent ring 12. However, connecting links 22 may connect a peak 16 of one ring 12 to a peak 16 of an adjacent ring, or a valley 18 to a valley 18, or a straight segment 20 to a straight segment 20. Further, connecting links 22 may be curved. Connecting links 22 may also be excluded, with a peak 16 of one ring 12 being directly attached to a valley 18 of an adjacent ring 12, such as by welding, soldering, or the manner in which stent 100 is formed, such as by etching the pattern from a flat sheet or a tube.

It will be appreciated by those of ordinary skill in the art that stent 100 of FIG. 1 is merely an exemplary stent and that stents of various forms and methods of fabrication can be used in accordance with various embodiments of the present invention. For example, in a typical method of making a stent, a thin-walled, small diameter metallic tube is cut to produce the desired stent pattern, using methods such as laser cutting or chemical etching. The cut stent may then be de-scaled, polished, cleaned and rinsed. Some examples of methods of forming stents and structures for stents are shown in U.S. Pat. No. 4,733,665 to Palmaz, U.S. Pat. No. 4,800,882 to Gianturco, U.S. Pat. No. 4,886,062 to Wiktor, U.S. Pat. No. 5,133,732 to Wiktor, U.S. Pat. No. 5,292,331 to Boneau, U.S. Pat. No. 5,421,955 to Lau, U.S. Pat. No. 5,935,162 to Dang, U.S. Pat. No. 6,090,127 to Globerman, and U.S. Pat. No. 6,730,116 to Wolinsky et al., each of which is incorporated by reference herein in its entirety. Further, balloon-expandable stents may also be utilized in various embodiments of the present invention, such as those disclosed in U.S. Pat. No. 5,776,161 to Globerman, U.S. Pat. No. 6,113,627 to Jang, and U.S. Pat. No. 6,663,661 to Boneau, each of which is incorporated by reference herein in its entirety.

In accordance with various embodiments of the present invention, an "active" or anodic metallic material 10, or an alloy thereof, is to be used in making the metallic substrate of the framework of stent 100. An anodic metallic material is one that possesses an electrical potential that is lower than a standard reference electrode, such as a saturated calomel electrode or SCE. The lower or more negative the electric potential relative to the standard reference electrode, the more "active" the metallic material is considered. In embodiments according to the present invention, a metallic material 10 for use as the stent substrate has a voltage potential in the range of −0.1 to −2.0 volts versus SCE. Such an "active" metal is one that is susceptible to corrosion or degradation through galvanic coupling, i.e., when coupled or contacted with a cathodic or noble material, as discussed in more detail below. Examples of such metals for use in embodiments of the present invention include, but are not limited to, magnesium, zinc, aluminum, nickel, and manganese, and alloys thereof, as well as active stainless steel alloys.

In the embodiment of FIG. 2, a biocompatible coating 26 is illustrated as disposed on an outer surface 24 of metallic material 10 of stent 100. Coating 26 is comprised of a biodegradable polymer 34 dispersed with particles 25 of a cathodic or noble metallic material. In an embodiment, the noble metallic material may be dispersed within the biodegradable polymer as a powder by any method known in the art. A cathodic metallic material is one that possesses an electrical potential that is higher than a standard reference electrode, such as the SCE mentioned above. The greater, or more positive, the electric potential relative to the standard reference electrode, the more noble or "inactive" the metallic material is considered. In embodiments according to the present invention, a noble metallic particulate 25 for use in the polymeric coating 26 has a voltage potential in the range of 1.0 to 3.5 volts versus SCE. Examples of noble metals, which are also radiopaque, for use in embodiments of the present invention include, but are not limited to, platinum, gold, titanium, silver, tantalum, and iridium, and alloys thereof.

After stent 100 is implanted within a body lumen, noble metallic particulate 25 within the coating 26 allow electrical conductivity with the anodic material 10 of the stent substrate, such that galvanic corrosion of the stent framework occurs. Therefore, a particulate count or density of noble metallic particulate 25 within the biodegradable polymer 34 must be great enough to facilitate this interaction, and may be increased or decreased in order to control the dissolution rate of the "active" metallic material 10 of the stent substrate. In an embodiment, after placement of the stent within the body lumen, biodegradable coating 26 must first at least partially degrade/erode before noble metallic particulate 25 are exposed, such that galvanic corrosion of the stent structure begins after a therapeutically appropriate period of time, which is the time period during which the full-strength of the stent structure is needed to restore patency to the vessel. In another embodiment, after placement of the stent within the body lumen, noble metallic particulate 25 are distributed within coating 26, such that galvanic corrosion of the stent structure occurs prior to erosion or degradation of coating 26.

Over time, the stent framework will be fully bioresorbed and the polymer coating completely degraded leaving no remnant of the stent structure or its material within the body lumen. In an embodiment, the "active" metallic material of the stent substrate is fully bioresorbed prior to the polymer coating completely degrading. In another embodiment, the polymer coating completely degrades before the "active" metallic material of the stent substrate is fully bioresorbed.

In an embodiment, the rate of degradation or bioresorbtion of the stent structure may be controlled by selecting the anodic and cathodic materials, i.e., the first and second metallic materials, to increase or decrease their relative potential. In another embodiment, the rate of degradation or bioresorbtion of the stent structure may be controlled by varying the exposed surface area of the stent substrate, wherein some surface areas are coated with the polymer and particulate material and other areas remain uncoated.

Examples of biodegradable polymers for use in embodiments of the present invention, include, but are not limited to: poly($\alpha$-hydroxy acids), such as, polycapro lactone (PCL), poly(lactide-co-glycolide) (PLGA), polylactide (PLA), and polyglycolide (PGA), and combinations and blends thereof, PLGA-PEG (polyethylene glycol), PLA-PEG, PLA-PEG-PLA, polyanhydrides, trimethylene carbonates, polyorthoesters, polyaspirins, polyphosphagenes, and tyrozine polycarbonates.

In the embodiment of FIG. 2, only outer surface 24 of metallic material 10 of the stent substrate is shown coated. By example, coating 26 may be of a thickness "C" in the range of 0.5-10 μm with the metallic material 10 of the stent substrate being of a thickness "T" in the range of 50-100 μm. However it should be understood that in various other embodiments, all or portions of outer surface 24, inner surface 28, and/or side surfaces 30 may be coated with coating 26, as may be desired to achieve an appropriate rate of degradation of the underlying metallic material 10 that makes-up the substrate of stent 100.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

The invention claimed is:

1. An endoluminal prosthesis for placement in a body lumen comprising:
a stent substrate comprised of a first metallic material that has a lower electrical potential than a standard reference electrode; and
a biocompatible coating disposed on the stent substrate, the coating being comprised of a biodegradable polymer having a second metallic material dispersed therein, wherein the second metallic material has a higher electrical potential than the standard reference electrode and is present in the coating in a sufficient particulate density to cause galvanic corrosion of the first metallic material after placement of the endoluminal prosthesis within the body lumen.

2. The endoluminal prosthesis of claim 1, wherein the standard reference electrode is one of a standard hydrogen electrode and a saturated calomel electrode.

3. The endoluminal prosthesis of claim 2, wherein the first metallic material is selected from a group consisting of magnesium, zinc, aluminum, stainless steel, nickel, and manganese, and alloys thereof.

4. The endoluminal prosthesis of claim 3, wherein the second metallic material is selected from a group consisting of platinum, gold, titanium, silver, tantalum, and iridium, and alloys thereof.

5. The endoluminal prosthesis of claim 4, wherein the second metallic material is dispersed within the coating as a powder.

6. The endoluminal prosthesis of claim 2, wherein the electrical potential of the first metallic material is in the range of −0.1 to −2.0 volts with respect to the saturated calomel electrode.

7. The endoluminal prosthesis of claim 6, wherein the electrical potential of the second metallic material is in the range of 1.0 to 3.0 volts with respect to the saturated calomel electrode.

8. The endoluminal prosthesis of claim 7, wherein the second metallic material is dispersed within the coating as a powder.

9. The endoluminal prosthesis of claim 1, wherein the stent substrate is bioresorbed due to the galvanic corrosion.

10. The endoluminal prosthesis of claim 9, wherein the stent substrate is fully bioresorbed prior to complete degradation of the biodegradable polymer coating.

11. The endoluminal prosthesis of claim 9, wherein the biodegradable polymer coating is completely degraded prior to the stent substrate being fully bioresorbed.

12. The endoluminal prosthesis of claim 1, wherein galvanic corrosion of the stent substrate begins a therapeutically appropriate period of time after placement of the prosthesis within the body lumen.

* * * * *

UNITED STATES PATENT AND TRADEMARK OFFICE
CERTIFICATE OF CORRECTION

PATENT NO. : 7,651,527 B2  Page 1 of 1
APPLICATION NO. : 11/611533
DATED : January 26, 2010
INVENTOR(S) : Krivoruchko et al.

It is certified that error appears in the above-identified patent and that said Letters Patent is hereby corrected as shown below:

Title Page, Item (75) Inventors: "Micheal Krivoruchko" should be changed to --Michael Krivoruchko--

Signed and Sealed this

Twenty-first Day of December, 2010

David J. Kappos
*Director of the United States Patent and Trademark Office*